United States Patent [19]

Wasley

[11] Patent Number: 4,882,339
[45] Date of Patent: Nov. 21, 1989

[54] 4-AMINO-SUBSTITUTED 1,2-DIHYDROXYNAPHTHALENE DERIVATIVES USEFUL IN INHIBITING 5-LIPOXYGENASE ACTIVITY IN MAMMALS

[75] Inventor: Jan W. F. Wasley, Chatham, N.J.

[73] Assignee: Ciba-Geigy Corporation, Ardsley, N.Y.

[21] Appl. No.: 71,956

[22] Filed: Jul. 10, 1987

[51] Int. Cl.$^4$ .......................................... A61K 31/445
[52] U.S. Cl. ....................................... 514/319; 514/617; 514/619; 514/629; 514/630; 514/648; 514/657; 514/58.1; 514/173; 514/174; 514/399; 546/144; 546/164; 546/165; 546/206; 548/491; 548/509; 548/954
[58] Field of Search ............... 514/657, 648, 319, 617, 514/619, 629, 630

[56] References Cited

U.S. PATENT DOCUMENTS

| 4,593,120 | 6/1986 | Jones et al. | 514/533 |
| 4,686,220 | 8/1987 | Medwid et al. | 514/227 |
| 4,771,061 | 9/1988 | Medwid et al. | 514/367 |

FOREIGN PATENT DOCUMENTS 2191999 12/1987 United Kingdom .

OTHER PUBLICATIONS

Bullock et al., "Chemical Abstracts", vol. 71, col. 80999m.
Ku et al., "Chemical Abstracts", vol. 109, 1988, col. 109:404d.
Matera et al., "Chemical Abstracts", vol. 109, 1988, col. 109:222198d.
Guilbault et al., Anal. Chem., 37, 1675–1680, (1965).
Lantz, Bull. Soc. Chim. France, 71, 249, (1971).
Ibrahm et al., J. Amer. Chem. Soc., 80, 6057, (1958).
Bullock et al., J. Chem. Soc.(C), 1799, (1969), pp. 1799–1803.
Bullock et al., J. Med. Chem., 13, 97, (1970), pp. 97–103.
Elslager et al., J. Med. Chem., 13, 104, (1970), pp. 104–109.
Chem. Abstracts, 81, 63389b, (1974).

Henri Goldstein et al., Helv. Chem., Acta 20, 1413–147, (1937).
S. Petersen et al., Z. Krebsforsch, 72, 162, (1969).
Y. Matsunaga, Bull. Chem. Soc., Japan, 52, 1211, (1979).
Goodman and Gilman's The Pharmacological Basis of Therapeutics, 7th Ed., Chapters 28 and 45.

Primary Examiner—Glennon H. Hollrah
Assistant Examiner—James H. Turnipseed
Attorney, Agent, or Firm—Norbert Gruenfeld

[57] ABSTRACT

Disclosed are compounds of the formula

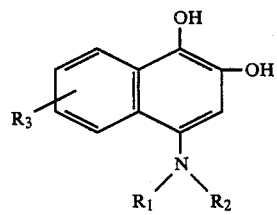

wherein $R_1$ represents unsubstituted or lower alkyl-substituted $C_3$–$C_7$-cycloalkyl, unsubstituted or lower alkyl substituted $C_7$-or $C_8$-bicycloalkyl, unsubstituted or lower alkyl-substituted adamantyl, 4-piperidinyl or N-lower alkyl or aryl-lower alkyl-substituted piperidinyl, 1- or 2-indanyl, 1- or 2-tetrahydronaphthyl, 1- or 2-perhydroindanyl, 1- or 2-perhydronaphthyl; $R_2$ represents hydrogen, lower alkyl, $C_3$–$C_7$-cycloalkyl, aryl-lower alkyl, $C_3$–$C_7$-cycloalkyl-lower alkyl, lower alkanoyl or aryl-lower alkanoyl; or $R_1$ and $R_2$ combined with the nitrogen to which they are attached represent pyrrolidino, piperidino, perhydroazepino, morpholino, thiomorpholino, tetrahydro- or perhydro-(isoquinolinyl or quinolinyl), dihydro- or perhydroindolyl, piperazino or N-lower alkyl-piperazino; $R_3$ represents hydrogen, lower alkyl, halogen or lower alkoxy; pharmaceutically acceptable ester and ether derivatives thereof; and pharmaceutically acceptable acid-addition salts of any said basic compounds of formula I and derivatives thereof; as 5-lipoxygenase inhibitors.

11 Claims, No Drawings

4-AMINO-SUBSTITUTED 1,2-DIHYDROXYNAPHTHALENE DERIVATIVES USEFUL IN INHIBITING 5-LIPOXYGENASE ACTIVITY IN MAMMALS

SUMMARY OF THE INVENTION

The invention relates to certain 4-amino-substituted-1,2-dihydroxynaphthalene derivatives and intermediates which are useful particularly as selective 5-lipoxygenase inhibitors, methods for preparation thereof, pharmaceutical compositions comprising said compounds, and a method of inhibiting 5-lipoxygenase and of treating diseases in mammals which are responsive to 5-lipoxygenase inhibition using said compounds or pharmaceutical compositions comprising said compounds of the invention.

The compounds of the invention, including certain intermediates, are particularly useful for the treatment of various inflammatory and allergic conditions, e.g. bronchial allergies and inflammatory disorders such as asthma, ocular allergies and inflammation, and dermatological allergies and inflammation such as psoriasis; also for the treatment of rheumatic disorders such as rheumatoid arthritis; and also for the treatment of ischemic conditions such as myocardial infarction and cerebral ischemia.

DETAILED DESCRIPTION OF THE INVENTION

More particularly the invention relates to the compounds of formula I

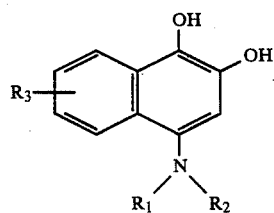

(I)

wherein $R_1$ represents unsubstituted or lower alkyl-substituted $C_3$-$C_7$-cycloalkyl, unsubstituted or lower alkyl substituted $C_7$- or $C_8$-bicycloalkyl, unsubstituted or lower alkyl-substituted adamantyl, 4-piperidinyl or N-lower alkyl or aryl-lower alkyl-substituted piperidinyl, 1- or 2-indanyl, 1- or 2-tetrahydronaphthyl, 1- or 2-perhydroindanyl, 1- or 2-perhydronaphthyl; $R_2$ represents hydrogen, lower alkyl, $C_3$-$C_7$-cycloalkyl, aryl-lower alkyl, $C_3$-$C_7$-cycloalkyl-lower alkyl, lower alkanoyl or aryl-lower alkanoyl; or $R_1$ and $R_2$ combined with the nitrogen to which they are attached represent pyrrolidino, piperidino, perhydroazepino, morpholino, thiomorpholino, tetrahydro- or perhydro-(isoquinolinyl or quinolinyl), dihydro- or perhydroindolyl, piperazino or N-lower alkyl-piperazino; $R_3$ represents hydrogen, lower alkyl, halogen or lower alkoxy; pharmaceutically acceptable ester and ether derivatives thereof; and pharmaceutically acceptable acid-addition salts of any said basic compounds of formula I and derivatives thereof.

The pharmaceutically acceptable ester derivatives represent compounds of formula I in which one or both hydroxy groups are esterified in the form of a pharmaceutically acceptable ester, particularly prodrug esters that may be convertible, e.g. by solvolysis under physiological conditions, to the compounds of formula I having free hydroxy groups. Such represent a preferred embodiment of the invention.

Suitable as prodrug pharmaceutically acceptable esters are lower alkanoic acid esters; lower alkoxy-lower alkanoic acid esters; arylcarboxylic acid esters; aryl-lower alkanoic acid esters; carbamic or N-mono- or N,N-di-(lower alkyl, aryl or aryl-lower alkyl)-carbamic acid esters (carbamates); phosphoric acid or O,O-di-(lower alkyl, aryl or aryl-loweralkyl)-phosphoric acid esters; carbonic acid or O-(lower alkyl, aryl or aryl-lower alkyl)-carbonic acid esters; the cyclic carbonic acid ester in which both ring hydroxy groups are esterified in form of a cyclic carbonate ester derivative; or a cyclic phosphoric acid ester in which both ring hydroxy groups are esterified in form of a cyclic phosphate ester derivative.

Pharmaceutically acceptable ether derivatives, in which one or both hydroxy groups are so derivatized, are preferably the mono- or di-lower alkyl or aryl-lower alkyl ethers, or the cyclic lower alkylene ethers (in which both vicinal hydroxy groups are etherified in form of a lower alkylenedioxy group).

Preferred as prodrug pharmaceutically acceptable esters are straight chain or branched lower alkanoic acid esters, e.g. the acetic, isobutyric, pivaloic acid esters; lower alkoxy-lower alkanoic acid esters, e.g. the methoxyacetic, 3-ethoxypropionic acid esters; arylcarboxylic acid esters, e.g. the benzoic, nicotinic acid esters; carbamic and mono- or di-lower alkyl or aryl carbamic acid esters (carbamates), e.g. the mono- or di-ethylcarbamic or N-mono- or di-methylcarbamic acid esters.

A particular embodiment of the invention is represented by the compounds of formula II

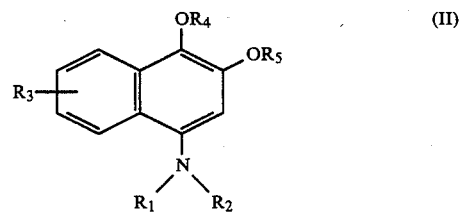

(II)

wherein $R_1$ represents $C_5$-$C_7$-cycloalkyl, bicyclo[2,2,1]heptyl, adamantyl, 1- or 2-indanyl or perhydroindanyl, or 1- or 2-tetrahydro- or perhydro-naphthyl; $R_2$ represents hydrogen, lower alkyl, aryl-lower alkyl, $C_5$-$C_7$-cycloalkyl-lower alkyl, lower alkanoyl or aryl-lower alkanoyl; $R_3$ represents hydrogen, lower alkyl or halogen; $R_4$ and $R_5$ independently represent hydrogen, lower alkanoyl, aroyl, lower alkyl, N-aryl-carbamoyl, N-mono- or N,N-di-alkyl carbamoyl, or O,O-di-lower alkylphosphonyl; or $R_4$ and $R_5$ together represent carbonyl; and pharmaceutically acceptable acid addition salts thereof provided $R_2$ represents hydrogen, lower alkyl, aryl-lower alkyl or $C_5$-$C_7$-cycloalkyl-lower alkyl.

Preferred are the said compounds of formula II wherein $R_1$ represents cyclopentyl, cyclohexyl, cycloheptyl, 2-norbornyl, 1- or 2-adamantyl, 1- or 2-indanyl or 1- or 2-perhydroindanyl; $R_2$ represents hydrogen, $C_1$-$C_4$-alkyl or aryl-$C_1$-$C_4$-alkyl; $R_3$ represents hydrogen, $C_1$-$C_4$-alkyl or halogen; $R_4$ represents hydrogen, $C_2$-$C_4$-alkanoyl, N-arylcarbamoyl, N-mono- or N,N-di-$C_1$-$C_4$-alkylcarbamoyl; $R_5$ represents hydrogen, $C_1$-$C_4$-alkyl, $C_2$-$C_4$-alkanoyl, N-arylcarbamoyl, N-mono- or N,N-di-$C_1$-$C_4$-alkylcarbamoyl, or O,O-di-$C_1$-$C_4$-alkylphosphonyl; and pharmaceutically acceptable acid addition salts thereof.

Most preferred are said compounds of formula II wherein $R_1$ represents cyclopentyl, cyclohexyl or cycloheptyl; $R_2$ represents lower alkyl, $R_3$ represents hydrogen; $R_4$ represents $C_2$–$C_4$-alkanoyl; $R_5$ represents $C_2$–$C_4$-alkanoyl; and pharmaceutically acceptable acid addition salts thereof.

Most particularly preferred are the compounds of formula II wherein $R_1$ represents cyclohexyl; $R_2$ represents $C_1$–$C_4$-alkyl; $R_3$ represents hydrogen; $R_4$ and $R_5$ represent $C_2$–$C_4$-alkanoyl; and pharmaceutically acceptable acid-addition salts thereof.

Another particular embodiment of the invention is directed to the compounds of the formula II wherein $R_1$ and $R_2$ combined with the nitrogen to which they are attached represent pyrrolidino, piperidino, perhydroazepino, morpholino, thiomorpholino, piperazino or N-lower alkyl-piperazino, tetrahydro- or perhydroisoquinolinyl, tetrahydro- or perhydro-quinolinyl, dihydro- or perhydroindolyl; $R_3$ represent hydrogen, lower alkyl or halogen; $R_4$ and $R_5$ independently represent hydrogen, lower alkanoyl, aroyl, lower alkyl, N-arylcarbamoyl, N-mono- or N,N-dialkylcarbamoyl or O,O-di-lower alkylphosphonyl; or $R_4$ and $R_5$ combined represent carbonyl; and pharmaceutically acceptable salts thereof.

Particularly preferred are said compounds of formula II wherein $R_1$ and $R_2$ combined with the nitrogen to which they are attached represent tetrahydro- or perhydro-isoquinolinyl, tetrahydro- or perhydroquinolinyl, dihydro- or perhydroindolyl; $R_3$ represents hydrogen; $R_4$ represents hydrogen, $C_2$–$C_4$-alkanoyl, N-arylcarbamoyl, N-mono or N,N-di-$C_1$–$C_4$-alkylcarbamoyl; $R_5$ represents hydrogen, $C_1$–$C_4$-alkyl, $C_2$–$C_4$-alkanoyl, N-arylcarbamoyl, N-mono- or N,N-di-$C_1$–$C_4$-alkylcarbamoyl, or O,O-di-$C_1$–$C_4$-alkylphosphonyl; and pharmaceutically acceptable acid-addition salts thereof.

Most preferred are said compounds of formula II wherein $R_1$ and $R_2$ combined with the nitrogen to which they are attached represent tetrahydroquinolinyl, perhydroquinolinyl, tetrahydroisoquinolinyl or perhydroisoquinolinyl; $R_3$ represents hydrogen; $R_4$ and $R_5$ represent $C_2$–$C_4$-alkanoyl; and pharmaceutically acceptable acid addition salts thereof.

The general definitions used herein have the following meaning within the scope of the present invention.

The term "lower" referred to above and hereinafter in connection with organic radicals or compounds respectively defines such as branched or unbranched with up to and including 7, preferably up to and including 4 and advantageously one or two carbon atoms.

A lower alkyl group preferably contains 1–4 carbon atoms and represents for example ethyl, propyl, butyl or advantageously methyl.

A lower alkoxy group preferably contains 1–4 carbon atoms and represents for example ethoxy, propoxy, isopropoxy or advantageously methoxy.

Lower alkanoyl represents preferably $C_2$–$C_4$-alkanoyl such as acetyl or propionyl.

Halogen preferably represents chloro or fluoro but may also be bromo or iodo.

An aryl radical (Ar) represents preferably a carbocyclic aryl radical.

A carbocyclic aryl radical represents preferably phenyl or phenyl mono- or di-substituted by one or two radicals selected from lower alkyl, lower alkoxy, halogen, cyano and trifluoromethyl; or 1- or 2-naphthyl.

Aroyl represents preferably benzoyl or benzoyl mono- or di-substituted by one or two radicals selected from lower alkyl, lower alkoxy, halogen, cyano and trifluoromethyl; or 1- or 2-naphthoyl.

Bicycloalkyl represents particularly unsubstituted or lower alkyl substituted bicyclo[2,2,1]heptyl, such as bornyl, neobornyl, isobornyl, norbornyl, e.g. 2-norbornyl, particularly 2-exo-norbornyl.

Tricycloalkyl represents particularly unsubstituted or lower alkyl substituted adamantyl, particularly 1- or 2-adamantyl.

Pharmaceutically acceptable salts of the basic compounds of the invention are acid addition salts, which are preferably such of therapeutically acceptable inorganic or organic acids, such as strong mineral acids, for example hydrohalic, e.g. hydrochloric or hydrobromic acid, sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric pyruvic, phenylacetic, benzoic, 4-aminobenzoic, anthranilic, 4-hydroxybenzoic, salicyclic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The compounds of the invention exhibit valuable pharmacological properties in mammals, and are particularly useful as selective 5-lipoxygenase inhibitors for the treatment of e.g. inflammatory and allergic conditions.

The above-cited properties are demonstrable in in vitro and in vivo tests, using advantageously mammals, e.g. rats, guinea pigs, dogs, rabbits or isolated organs, tissues, and enzyme preparations thereof, as well as cells and fluids isolated from mammalian, including human, blood. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-4}$ molar and $10^{-9}$ molar concentrations. The dosage in vivo may range depending on the route of administration, between about 0.01 and 25 mg/kg.

5-HETE and various leukotriene products are formed from arachidonic acid by means of the enzyme 5-lipoxygenase. Leukotrienes (LTs) $B_4$, $C_4$, $D_4$ and $E_4$ are a group of mediators with potent leukocyte-chemoattractant, smooth muscle-constricting and vascular permeability-enhancing properties. $LTB_4$ is among the most potent leukocyte chemotactic agents known. $LTC_4$, $LTD_4$ and $LTE_4$ are the components of the "slow-reacting substance of anaphylaxis" (SRS-A) and are potent inducers of broncho-constriction that are released during an antigen challenge in lungs. Leukotrienes have been implicated in the pathogenesis of a variety of vascular and pulmonary disorders involving leukocyte and smooth muscle activation. Since these products are derived from the biotransformation of arachidonic acid (AA) through the 5-lipoxygenase pathway, selective inhibition of 5-lipoxygenase will suppress their formation in leukocytes and various organ systems.

5-Lipoxygenase inhibition is determined e.g. by measuring the percent inhibition of the synthesis of 5-HETE [(5S)-5-hydroxy-6,8,11,14-eicosa-tetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, essentially according to radiometric thin-layer chromatogrpahic assays described by Walker and Dawson (J. Pharm. Pharmacol. 31: 778, 1979) and Jakschik and Lee (Nature 287: 51, 1980) used to measure the formation of 5-HETE and LTB$_4$-like products from $^{14}$C-arachidonic acid. IC$_{50}$ values are determined graphically as the concentration of test compound at which the synthesis of 5-HETE and LTB$_4$-like products is reduced to 50% of their respective control values.

Furthermore the inhibition of 5-lipoxygenase in vivo is determined after oral or i.v. administration to rats or dogs by measuring ex vivo in whole blood the inhibition of A-23187-stimulated LTB$_4$ formation as compared to non-treated control animals.

Antiinflammatory activity is demonstrated by measuring the inhibition of the edema and of the leukocyte influx after oral administration in the rat model in which pleurisy is first induced by injecting carrageenin into the pleural cavity, e.g. according to A. P. Almeida et al., J. Pharmacol. Exp. Therap. 214, 74 (1980).

Illustrative of the invention 4-(N-methylcyclohexylamino)-1,2-diacetoxynaphthalene inhibits the formation of 5-HETE [(5S)-5-hydroxy-6,8,11,14-eicosa-tetraenoic acid] and leukotriene B$_4$ (LTB$_4$, 5,12-dihydroxy-6,8,10,14-eicosatetraenoic acid) in A-23187-stimulated guinea pig polymorphonuclear leukocytes, e.g. at an IC$_{50}$ of about one micromolar ($1 \times 10^{-6}$M) for LTB$_4$ formation. Said compound also inhibits 5-lipoxygenase activity as determined ex vivo when administered at a dose of 1 mg/kg i.v. or 100 mg/kg p.o. in the dog and in the rat at a dose of about 10–100 mg/kg p.o.

Furthermore, 4-(N-methylcyclohexylamino)-1,2-diacetoxynaphthalene at 30 mg/kg p.o. administered b.i.d. for two days, causes inhibition of exudate volume and lowers the cell count of polymorphonuclear leukocytes and of monocytes 48 hours after injection of carrageenin in the rat pleurisy model of inflammation.

The compounds of the invention are thus useful, particularly for the treatment and amelioration of diseases and conditions in mammals, including man, in which lipoxygenase activity or the accumulation of leukocytes (e.g. neutrophils) is involved, particularly allergic and inflammatory disorders, e.g. pulmonary allergies and inflammatory disorders such as asthma, dermatological allergies and inflammatory disorders such as psoriasis, also arthritic inflammatory disorders such as rheumatoid arthritis, and ocular allergies and inflammatory disorders, as well as ischemic conditions such as in myocardial infarction.

The compounds of the invention can be prepared by synthetic processes comprising:

(a) reducing a compound of the formula III

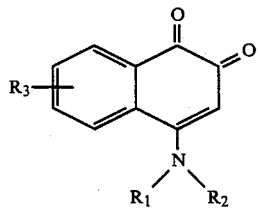

wherein R$_1$, R$_2$ and R$_3$ have the meanings given above, with a suitable reducing agent to a compound of formula I and converting a so-obtained compound of formula I to an ester derivative thereof as defined above or to another compound of the invention; or (b) for compounds of the invention wherein R$_1$ and R$_2$ are not combined with N to form a cyclic substituent, reducing a compound of the formula IV

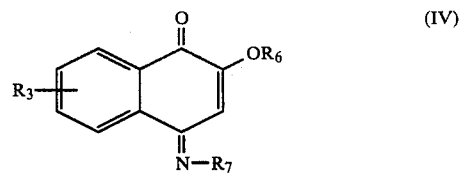

wherein R$_6$ represents lower alkyl or aryl-lower alkyl, and R$_7$ represents a substituent as defined e.g. for R$_1$ in formula II above, and R$_3$ has meaning as defined above to obtain a compound of formula V

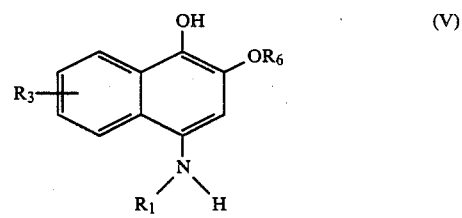

wherein R$_1$, R$_3$ and R$_6$ have meaning as defined above, and then converting said compound of formula V to another compound of the invention, e.g. wherein the free hydroxy group is esterified and/or wherein R$_2$ is a substituent other then hydrogen.

In the above cited processes, the said process is carried out while, if necessary, temporarily protecting any interfering reactive group(s), and then liberating the resulting compound of the invention; and, if required or desired, a resulting compound of the invention is converted into another compound of the invention, and/or, if desired, a resulting free compound is converted into a salt or a resulting salt is converted into the free compound or into another salt; and/or a mixture of isomers or racemates obtained is separated into the single isomers or racemates; and/or, if desired, a racemate is resolved into the optical antipodes.

In starting compounds and intermediates therefor which are converted to the compounds of the invention in a manner described herein, functional groups present, such as amino and hydroxy groups, are optionally protected by conventional protecting groups that are common in preparative organic chemistry. Protected amino and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1984.

The reduction according to process (a) is carried out according to procedures known in the art for converting ortho-quinone type compounds to the corresponding vicinal aromatic diols. The reduction is preferably carried out using hydrogenation, with hydrogen in the presence of a suitable catalyst, such as palladium on charcoal in a solvent such as dichloromethane. The compounds of the invention are preferably isolated with one or both hydroxy groups in protected form. The hydrogenation is preferably carried out at atmospheric or elevated pressure and room temperature. Furthermore, the reduction of compound of formula III is preferably carried out in the presence of an acrylating reagent so as to directly obtain a compound of the invention in which one or both hydroxy groups in formula I are esterified as indicated hereinabove. When appropriate the acylating reagent, e.g. acetic anhydride, is used as the solvent for the hydrogenation reaction.

Acrylating reagents are those generally known in the art for preparing esters as defined above.

Suitable acrylating reagents are for example acid anhydrides or halides to obtain the lower alkanoic acid, aryl carboxylic acid, aryl-lower alkanoic acid and lower alkoxy-lower alkanoic acid esters, isocyanates to obtain the mono (lower alkyl, aryl or aryl-lower alkyl)-carbamic acid esters, N,N-disubstituted carbamoyl chlorides to obtain di-(lower alkyl, aryl or aryl-lower alkyl)-carbamic acid esters, 1,1'-carbonyldiimidazole to obtain esters in which both hydroxy groups are esterified in form of a cyclic carbonate ester.

In a particular aspect of process (a), the reduction can be carried out with a tri-(lower alkyl) phosphite such as triethyl phosphite to yield directly a di-(lower alkyl) phosphoric acid ester of a compound of formula I.

The starting materials of formula III are prepared according to methods known in the art by reacting a 1,2-naphthoquinone derivative of formula VI

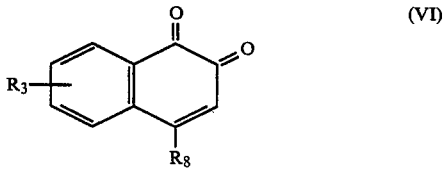

(VI)

wherein $R_8$ represents a leaving group, with an amine of the formula VII

(VII)

wherein $R_1$ and $R_2$ independently or combined have meaning as defined above.

A leaving group $R_8$ is e.g. chloro, bromo or iodo, and preferably the sulfonic acid group as its sodium or potassium salt; $R_8$ may also be lower alkoxy, e.g. ethoxy.

The preparation of the said intermediates of the formula III, is preferably carried out by reacting a salt, preferably an alkali metal salt, e.g. a sodium salt of an optionally substituted 1,2-naphthoquinone-4-sulfonic acid (a compound of formula VI wherein the leaving group $R_8$ is $SO_3Na$) in a suitable solvent, preferably water, at a temperature between about +5° C. and +90° C., preferably at room temperature, with an amine of the formula VII.

The amines of formula VII are known in the art or are prepared according to methods well-known in the art. Similarly the 1,2-naphthoquinone derivatives of formula VI are known in the art or are prepared according to methods well-known in the art.

The reduction according to process (b) is essentially carried out as described for process (a). In the resulting compound of formula V, the free hydroxy group can be either acylated as described above or alkylated according to methods well-known in the art. Furthermore, in said compounds of formula V, the secondary amino group can also be subsequently either N-acrylated, e.g. in the presence of zinc chloride, to obtain compounds of the invention in which $R_2$ represents lower alkanoyl or aryl-lower alkanoyl or N-alkylated to obtain compounds of the invention wherein $R_2$ represents e.g. lower alkyl or aryl-lower alkyl.

The N-alkylation is carried out according to N-alkylation procedures well-known in the art, e.g. by condensation with a reactive derivative of the corresponding lower alkyl or aryl-lower alkyl alcohol, e.g. a halide such as the bromo or iodo derivative, either as such or in the presence of a base such as triethylamine or pyridine in an inert solvent, e.g. acetonitrile or dichloromethane, at room temperature or near the boiling point of the solvent used.

The starting materials of formula IV are preferably prepared by treating a compound of formula III wherein $R_2$ represents hydrogen (i.e. the 2-hydroxy-4-imino tautomeric form thereof) in alkaline solution, e.g. 30% aqueous sodium hydroxide, with e.g. a reactive derivative of a lower alkanol, such as a di-lower alkyl sulfate, for instance dimethyl sulfate.

Furthermore, the dihydroxy substituted compounds of formula I are converted, preferably in situ in view of their relative instability, to other compounds of the invention using methods generally known in the art.

For example, a compound of formula I can be converted to an ester derivative thereof, particularly a diester derivative as already described under process (a) above. A compound of formula I can also be converted to an ether derivative, particularly the diether derivatives under conditions generally known for the etherification of phenols, e.g. in the presence of a base, such as aqueous sodium hydroxide, in an inert atmosphere with a suitable etherifying reagent, particularly a reactive ester of the corresponding etherifying alcohol, such as a di-lower alkyl sulfate or a lower alkyl halide.

Conversely, a compound of the invention being an ester derivative of a compound of formula I can be converted to a compound of formula I under an inert atmosphere, e.g. by means of a dilute mineral acid at room temperature, such as dilute hydrochloric acid.

In addition, as already mentioned above, a compound of the invention wherein one of $R_1$ and $R_2$ represents hydrogen can be converted to a compound wherein the nitrogen is acylated by lower alkanoyl or aryl-lower alkanoyl by reacting such with e.g. the corresponding acid anhydride, preferably in the presence of a suitable Lewis acid such as anhydrous zinc chloride.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Advantageously those starting materials are used in said reactions that lead to the formation of those compounds indicated above as being preferred.

The invention also relates to any novel starting materials and processes for their manufacture.

Depending on the choice of starting materials and methods, the new compounds may be in the form of one of the possible isomers or mixtures thereof, for example, depending on the number of asymmetrical carbon atoms, as pure optical isomers, such as antipodes, as racemates or as mixtures of diastereoisomers. The aforesaid possible isomers or mixtures thereof are within the purview of this invention.

Any resulting mixtures of isomers can be separated on the basis of the physico-chemical differences of the constituents, in known manner, into the pure optical isomers, diastereoisomers, racemates, for example by chromatography and/or fractional crystallization.

Any resulting racemates can be resolved into the optical antipodes by known methods, e.g. by separation of the diastereoisomeric salts thereof, obtained with an optically active acid, and liberating the optically active basic compound by treatment with a standard base. Racemic products of the invention can thus be resolved into their optical antipodes, e.g., by the functional crystallization of d- or l-(tartrate, mandelate or camphorsulfonate) salts. Advantageously, the more active of the two antipodes is isolated.

Finally the compounds of the invention are either obtained in the free form, or as a salt thereof. Any resulting base can be converted into a corresponding acid addition salt, preferably with the use of a therapeutically useful acid or anion exchange preparation, or a resulting salt can be converted into the corresponding free base, for example, with the use of a stronger base, such as a metal or ammonium hydroxide or a basic salt, e.g. an alkali metal hydroxide or carbonate, or a cation exchange preparation, or an alkylene oxide such as propylene oxide. These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The 1,2-naphthoquinone intermediates of formula III and pharmaceutically acceptable salts thereof are also active as selective lipoxygenase inhibitors, and are thus useful as described above relating to the compounds of formula I and derivatives thereof; their pharmacological effects are also demonstrated in the manner described hereinabove for said compounds.

An aspect of the invention is therefore directed to the compounds of formula III as lipoxygenase inhibitors, in particular to their use as enumerated above (for the compounds of formula I and derivatives thereof), comprising the compounds of formula III wherein $R_1$ represents $C_5$-$C_7$-cycloalkyl, bicyclo[2,2,1]heptyl, adamantyl, 1- or 2-indanyl or perhydroindanyl, or 1- or 2-tetrahydro- or perhydro-naphthyl; $R_2$ represents hydrogen, lower alkyl, aryl-lower alkyl, $C_5$-$C_7$-cycloalkyl-lower alkyl, lower alkanoyl or aryl-lower alkanoyl; or $R_1$ and $R_2$ combined with the nitrogen to which they are attached represent pyrrolidino, piperidino, perhydroazepino, morpholino, thiomorpholino, piperazino or N-lower alkyl-piperazino, tetrahydro- or perhydro-isoquinolinyl, tetrahydro- or perhydro-quinolinyl, dihydro- or perhydroindolyl; $R_3$ represents hydrogen, lower alkyl or halogen; and pharmaceutically acceptable acid addition salts thereof.

A preferred embodiment is directed to the compounds of formula III wherein $R_1$ represents cyclopentyl, cyclohexyl, cycloheptyl, 2-norbornyl, 1- or 2-adamantyl, 1- or 2-indanyl or 1- or 2-perhydroindanyl; $R_2$ represents hydrogen, $C_1$-$C_4$-alkyl or aryl-$C_1$-$C_4$-alkyl; and $R_3$ represents hydrogen; and pharmaceutically acceptable acid addition salts thereof.

A further preferred embodiment is directed to the compounds of formula III wherein $R_1$ and $R_2$ combined with the nitrogen to which they are attached represent tetrahydro- or perhydroisoquinolinyl, tetrahydro- or perhydroquinolinyl, dihydro- or perhydroindolyl; and $R_3$ represents hydrogen; and pharmaceutically acceptable acid addition salts thereof.

Illustrative of the biological activity of the 1,2-naphthoquinone intermediates of formula III, 4-(N-methylcyclohexylamino)-1,2-naphthoquinone inhibits the formation of $LTB_4$ in A-23187-simulated guinea pig polymorphonuclear leukocytes at an $IC_{50}$ of about 0.5 micromolar in vitro.

Furthermore, the said intermediate, 4-(N-methylcyclohexylamino)-1,2-naphthoquinone, has also been identified as an in vivo metabolite of 4-(N-methylcyclohexylamino)-1,2-diacetoxynaphthalene, after administration of the latter.

The pharmaceutical compositions according to the invention are those suitable for enteral, such as oral or rectal, transdermal and parenteral administration to mammals, including man, to inhibit 5-lipoxygenase and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include adsorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The invention also relates to a method of inhibiting 5-lipoxygenase activity in mammals and treating diseases and conditions responsive thereto, particularly inflammatory and allergic disorders, using an effective amount of a compound of the invention as a pharmacologically active substance, preferably in the form of above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 10 and 200 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR).

EXAMPLE 1

A suspension of 3.5 g of 4-(N-methylcyclohexylamino)-1,2-naphthoquinone in 50 ml of acetic anhydride is hydrogenated at 45 lbs pressure and room temperature using 1.2 g of 10% palladium on carbon as catalyst. After uptake of hydrogen ceases and the red color of the solution is discharged (5 hours) the catalyst is removed by filtration. The acetic anhydride is evaporated under reduced pressure at 60° C. and the residue is taken up in toluene, treated with charcoal and filtered. The toluene solution is evaporated under reduced pressure and the product crystallized from 1:1 hexane-diethyl ether (100 ml) to afford 4-(N-methylcyclohexylamino)-1,2-diacetoxynaphthalene, the compound of formula II wherein $NR_1R_2$ represents N-methylcyclohexylamino, $R_3$ represents hydrogen, and $R_4$ and $R_5$ represent acetyl, m.p. 103°–105° C.; hydrochloride salt, m.p. 165°–167° C.

The starting material is prepared as follows:

A solution of 10.4 g of 1,2-naphthoquinone-4-sulfonic acid-sodium salt in 350 ml of water is stirred at room temperature for 30 minutes. To this solution is added 4.52 g of N-methylcyclohexylamine in one portion. The solution is stirred five hours at room temperature and the precipitate then filtered. The product is washed with 200 ml of water and dried at 100° C. in vacuo overnight to afford 4-(N-methylcyclohexylamino)-1,2-naphthoquinone melting at 168°–170° C. The preparation of the same compound from 4-ethoxy-1,2-naphthoquinone is reported in J. Med. Chem. 13, 97 (1970).

EXAMPLE 2

Prepared essentially as described in Example 1 are the following compounds of formula II wherein $R_4$ and $R_5$ represent acetyl, $R_3$ represents hydrogen and $NR_1R_2$ has meaning as defined below.

| $NR_1R_2$ | m.p. (°C.) |
|---|---|
| (a) N—ethylcyclohexylamino | 95–97° |
| (b) tetrahydroisoquinolinyl | 133–135° |
| (c) perhydroisoquinolinyl | 114–116° |
| (d) perhydroquinolinyl | 143–145° |
| (e) N—methylcycloheptylamino | 93–95° |
| (f) N—methyl-exo-2-norbornylamino | 105–107° |
| (g) N—methyl-1-indanylamino | 142–144° |
| (h) 1-adamantylamino | 84–86° |
| (i) 2-adamantylamino | 117–120° |
| (j) tetrahydroquinolinyl | — |
| (k) N—(1-methylpiperidin-4-yl)-methylamino | — |
| (l) cyclohexylamino | — |

The starting materials are the corresponding 1,2-naphthoquinones of formula III wherein $R_3$ represents hydrogen and $NR_1R_2$ has meaning as defined below.

| $NR_1R_2$ | m.p. (°C.) |
|---|---|
| (a) N—ethylcyclohexylamino | — |
| (b) tetrahydroisoquinolinyl | 256–258° |
| (c) perhydroisoquinolinyl | 251–253° |
| (d) perhydroquinolinyl | 223–225° |
| (e) N—methylcycloheptylamino | 260° |
| (f) N—methyl-exo-2-norbornylamino | 138–140° |
| (g) N—methyl-1-indanylamino | 258–260° |
| (h) 1-adamantylamino | above 180° |
| (i) 2-adamantylamino | — |
| (j) tetrahydroquinolinyl | above 250° |
| (k) N—(1-methylpiperidin-4-yl)-methylamino | 183–185° |
| (l) cyclohexylamino | 220–222° |

EXAMPLE 3

(a) A solution of 3.0 g of 4-(N-methylcyclohexylamino)-1,2-naphthoquinone and 4.8 g of 1,1'-carbonyldiimidazole in 150 ml of dichloromethane is hydrogenated at 45 lbs (3 atmospheres) pressure and room temperature using 1.5 g of 10% palladium on carbon as catalyst. After uptake of hydrogen ceases and the red color of the solution is discharged (5 hours), the catalyst is removed by filtration. The dichloromethane is evaporated under reduced pressure and the residue is stirred for 16 hours in 250 ml of diethyl ether and 150 ml of water. The organic phase is separated and washed with 100 ml of brine and then dried over magnesium sulfate and filtered. The diethyl ether is evaporated under reduced pressure and the residue is taken up in 200 ml of dichloromethane and filtered through 100 g of silica gel. The product is crystallized from 50 ml of diethyl ether to yield 4-(N-methylcyclohexylamino)-1,2-carbonyl-dioxy-naphthalene, m.p. 132°–134° C.

(b) Similarly prepared from 4-(N-methylcyclohexylamino)-1,2-naphthoquinone but using 5 moles of p-chlorophenylisocyanate as the acylating agent is 4-(N-methylcyclohexylamino)-1-(N-p-chlorophenylcarbamoyloxy)-2-hydroxynaphthalene, m.p. 108°–110° C.

(c) Similarly prepared to example (b) from 4-(N-methylcyclohexylamino)-1,2-naphthoquinone but hydrogenating the reaction mixture at room temperature for 20 hours, is 4-(N-methylcyclohexylamino)-1,2-di-(N-p-chlorohexylcarbamoyloxy)-naphthalene, m.p. 173°–175° C.

EXAMPLE 4

A solution of 3.0 g of 4-(N-methylcyclohexylamino)-1,2-naphthoquinone in 150 ml of dichloromethane is stirred at room temperature for 20 minutes. To this solution is added an excess of triethyl phosphite (8.5 ml). The solution is stirred for six hours and then 150 ml of water is added. The two phase reaction is stirred vigorously for 16 hours at room temperature.

The organic phase is separated, washed with 100 ml of brine, dried over magnesium sulfate and filtered. The dichloromethane is evaporated under reduced pressure and the residue taken up in hexane, treated with charcoal and filtered. The 4-(N-methylcyclohexylamino)-1-hydroxy-2-(diethylphosphonyloxy)-naphthalene was crystallized from 100 ml of hexane; m.p. 134°–136° C.

EXAMPLE 5

A suspension of 4-cyclohexylimino-1-oxo-2-methoxy-1,4-dihydronaphthalene in acetic anhydride is hydrogenated according to the procedure in Example 1 to obtain 4-cyclohexylamino-1-acetoxy-2-methoxynaphthalene, m.p. 134°–136° C.

The starting material is prepared as follows:

A solution of 9.0 g of 4-(cyclohexylamino)-1,2-naphthoquinone in 200 ml of dimethyl sulfate and 460 ml of 30% aqueous sodium hydroxide is heated slowly to reflux. The reaction mixture is stirred for 6 hours, washed with 300 ml of water and dried at 80° C. under vacuo to yield 4-cyclohexylimino-1-oxo-2-methoxy-1,4-dihydronaphthalene, m.p. 145°–147° C.

EXAMPLE 6

A solution 5.0 g of 4-(cyclohexylamino)-1-acetoxy-2-methoxynaphthalene in 75 ml of acetic anhydride is stirred with 500 mg of zinc chloride in at 160°–170° C. for 2 hours. The reaction is cooled, filtered and evaporated under reduced pressure. The residue is taken up in 300 ml of diethyl ether and washed with 100 ml of water and then with 100 ml of brine. The organic solvent is dried over magnesium sulfate, filtered, and evaporated to dryness. The residue is crystallized from 120 ml of 2:1 diethyl ether-hexane to yield 4-(N-acetylcyclohexylamino)-1-acetoxy-2-methoxynaphthalene, m.p. 137°–139° C.

EXAMPLE 7

(a) Preparation of 10,000 tablets each containing 10 mg of the active ingredient:
Formula:

| | |
|---|---|
| 4-(N—methylcyclohexylamino)-1,2-diacetoxynaphthalene hydrochloride | 100.00 g |
| Lactose | 2,400.00 g |
| Corn starch | 125.00 g |
| Polyethylene glycol 6,000 | 150.00 g |
| Magnesium stearate | 40.00 g |
| Purified water | q.s |

Procedure:

All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

(b) Preparation of 1,000 capsules each containing 10 mg of the active ingredient:
Formula:

| | |
|---|---|
| 4-(N—methylcyclohexylamino)-1,2-diacetoxynaphthalene hydrochloride | 10.0 g |
| Lactose | 207.0 g |
| Modified starch | 80.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

What is claimed is:

1. A method of inhibiting 5-lipoxygenase activity in mammals which comprises administering to a mammal in need thereof an effective 5-lipoxygenase inhibiting amount of a compound of the formula III

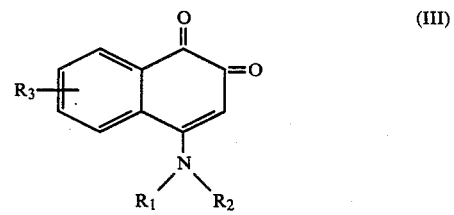

wherein $R_1$ represents unsubstituted or lower alkyl-substituted $C_3$–$C_7$-cycloalkyl, unsubstituted or lower alkyl substituted $C_7$- or $C_8$-bicycloalkyl, unsubstituted or lower alkyl-substituted adamantyl, 4-piperidinyl or N-lower alkyl or aryl-lower alkyl-substituted piperidinyl, 1- or 2-indanyl, 1- or 2-tetrahydronaphthyl, 1- or 2-perhydroindanyl, 1- or 2-perhydronaphthyl; $R_2$ represents hydrogen, lower alkyl, $C_3$–$C_7$-cycloalkyl, aryl-lower alkyl, $C_3$–$C_7$-cycloalkyl-lower alkyl, lower alkanoyl or aryl-lower alkanoyl; $R_3$ represents hydrogen, lower alkyl, halogen or lower alkoxy; aryl in the above definitions represents phenyl or phenyl mono- or di-substituted by one or two radicals selected from lower alkyl, lower alkoxy, halogen, cyano and trifluoromethyl, or aryl represents 1- or 2-naphthyl; or a pharmaceutically acceptable acid-addition salt of any said basic compound of formula III; or of a pharmaceutical composition comprising any said compound in combination with one or more pharmaceutically acceptable carriers.

2. A method according to claim 1 wherein, in a compound of formula III, $R_1$ represents $C_5$–$C_7$-cycloalkyl, bicyclo[2,2,1]heptyl, adamantyl, 1- or 2-indanyl or perhydroindanyl, or 1- or 2-tetrahydro- or perhydronaphthyl; $R_2$ represents hydrogen, lower alkyl, aryl-lower alkyl, $C_5$–$C_7$-cycloalkyl-lower alkyl, lower alkanoyl or aryl-lower alkanoyl; $R_3$ represents hydrogen, lower alkyl or halogen; aryl in the above definitions represents phenyl or phenyl mono- or di-substituted by one or two radicals selected from lower alkyl, lower alkoxy, halogen, cyano and trifluoromethyl; or a pharmaceutically acceptable acid addition salt thereof.

3. A method according to claim 1 wherein, in a compound of formula III, $R_1$ represents cyclopentyl, cyclohexyl, cycloheptyl, 2-norbornyl, 1- or 2-adamantyl, 1- or 2-indanyl or 1- or 2-perhydroindanyl; $R_2$ represents hydrogen, $C_1$–$C_4$-alkyl or aryl-$C_1$–$C_4$-alkyl; aryl in the above definitions represents phenyl or phenyl mono- or di-substituted by one or two radicals selected from lower alkyl, lower alkoxy, halogen, cyano and trifluoromethyl; and $R_3$ represents hydrogen; or a pharmaceutically acceptable acid addition salt thereof.

4. A method according to claim 1 wherein the compound of formula III is 4-(N-methylcyclohexylamino)-1,2-naphthoquinone or a pharmaceutically acceptable acid addition salt thereof.

5. A method according to claim 1 wherein the compound of formula III is 4-(N-methylcycloheptylamino)-1,2-naphthoquinone or a pharmaceutically acceptable acid addition salt thereof.

6. A method according to claim 1 wherein the compound of formula III is 4-(N-methyl-exo-2-norbornylamino)-1,2-naphthoquinone or a pharmaceutically acceptable acid addition salt thereof.

7. A method according to claim 1 wherein the compound of formula III is 4-(N-methyl-1-indanylamino)-1,2-naphthoquinone or a pharmaceutically acceptable acid addition salt thereof.

8. A method according to claim 1 wherein the compound of formula III is 4-(1-adamantylamino)-1,2-naphthoquinone or a pharmaceutically acceptable acid addition salt thereof.

9. A method according to claim 1 wherein the compound of formula III is 4-cyclohexylamino-1,2-naphthoquinone or a pharmaceutically acceptable acid addition salt thereof.

10. A method according to claim 1 wherein the compound of formula III is 4-[N-(1-methylpiperidin-4-yl)-methylamino]-1,2-naphthoquinone or a pharmaceutically acceptable acid addition salt thereof.

11. A method of treating inflammatory and allergic disorders responsive to the inhibition of 5-lipoxygenase in mammals, which comprises administering to a mammal in need thereof an effective 5-lipoxygenase inhibiting amount of a compound of the formula III

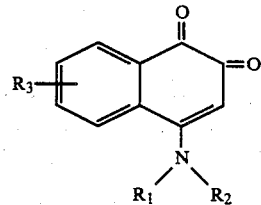

(III)

wherein $R_1$ represents unsubstituted or lower alkyl-substituted $C_3$–$C_7$-cycloalkyl, unsubstituted or lower alkyl substituted $C_7$- or $C_8$-bicycloalkyl, unsubstituted or lower alkyl-substituted adamantyl, 4-piperidinyl or N-lower alkyl or aryl-lower alkyl-substituted piperidinyl, 1- or 2-indanyl, 1- or 2-tetrahyronaphthyl, 1- or 2-perhydroindanyl, 1- or 2-perhydronaphthyl; $R_2$ represents hydrogen, lower alkyl, $C_3$–$C_7$-cycloalkyl, aryl-lower alkyl, $C_3$–$C_7$-cycloalkyl-lower alkyl, lower alkanoyl or aryl-lower alkanoyl; $R_3$ represents hydrogen, lower alkyl, halogen or lower alkoxy; or a pharmaceutically acceptable acid-addition salt of any said basic compound of formula III; or of a pharmaceutical composition comprising any said compound in combination with one or more pharmaceutically acceptable carriers.

* * * * *